US00PP11112P

United States Patent [19]

Princen et al.

[11] Patent Number: Plant 11,112

[45] Date of Patent: Nov. 2, 1999

[54] APPLE TREE NAMED 'RED JONAPRINCE'

[75] Inventors: Wilhelmus J. F. A. Princen; Antonius F. M. J. Princen, both of Weert, Netherlands

[73] Assignee: Wilton Weert B.V., Netherlands

[21] Appl. No.: 08/914,627

[22] Filed: Aug. 19, 1997

[51] Int. Cl.[6] ..... A01H 5/00

[52] U.S. Cl. ..... Plt./163

[58] Field of Search ..... Plt./34.1, 160, Plt./163

[56] References Cited

PUBLICATIONS

UPOVROM, Disk 98/01, 'Red Jonaprince', PLP 9603147, Hungary, 1996.

UPOVROM, Disk 98/01, 'Red Jonaprince'. PBR APP0200, New Zealand, 1995.

*Primary Examiner*—Howard J. Locker
*Assistant Examiner*—Melissa L. Kimball
*Attorney, Agent, or Firm*—Webb Ziesenheim Logsdon Orkin & Hanson, P.C.

[57] ABSTRACT

Red Jonaprince is a mutation of Jonagold having a bright to dark red colored, non-greasy and very early ripening apple. The fruit flesh is firmer and has a little more sugar and is a little more sour than that of Jonagold.

3 Drawing Sheets

BACKGROUND OF THE INVENTION

This discovery relates to a new and distinct variety of apple tree identified by the varietal name of Red Jonaprince. The new variety, which is a naturally occurring mutation of a Jonagold tree, an unpatented cultivar, was discovered as a whole plant in the discoverers' orchard in Weert, The Netherlands in 1994.

The fruit of the new variety has a non-greasy, smooth skin, distinctive yellow-brown lenticels, no stripes, a red stalk regardless of fruit color, and is about 98 percent red colored at picking time. The new variety is sufficiently mature at one year to produce fruit for consumption and all of the fruit has the same color on the same day. The leaf stalk is red up to the veins. The fruit has a little more sugar, is a little more sour and has firmer flesh than Jonagold, and is ready for picking four to five weeks earlier than Jonagold. The yield of Red Jonaprince is similar to that of Jonagold, the bearing habit is annual and the tree is spur bearing. There is no russetting with respect to the fruit. The fruit is suitable for the fresh fruit market. At the end of the flowering period, the receptacle is more intensely colored (purple red) than Jonagold's receptacle (soft pink red).

The new variety has been propagated by grafting onto root stocks of existing varieties including M9 and MM106. This grafting produced fruit with the same distinctive characteristics. There are now second generation trees bearing fruit.

DESCRIPTION OF THE DRAWINGS

The accompanying photographic drawings illustrate the new variety, with color being as nearly true as is possible with color illustrations of this type.

DESCRIPTION OF THE PLANT

Figure 1:
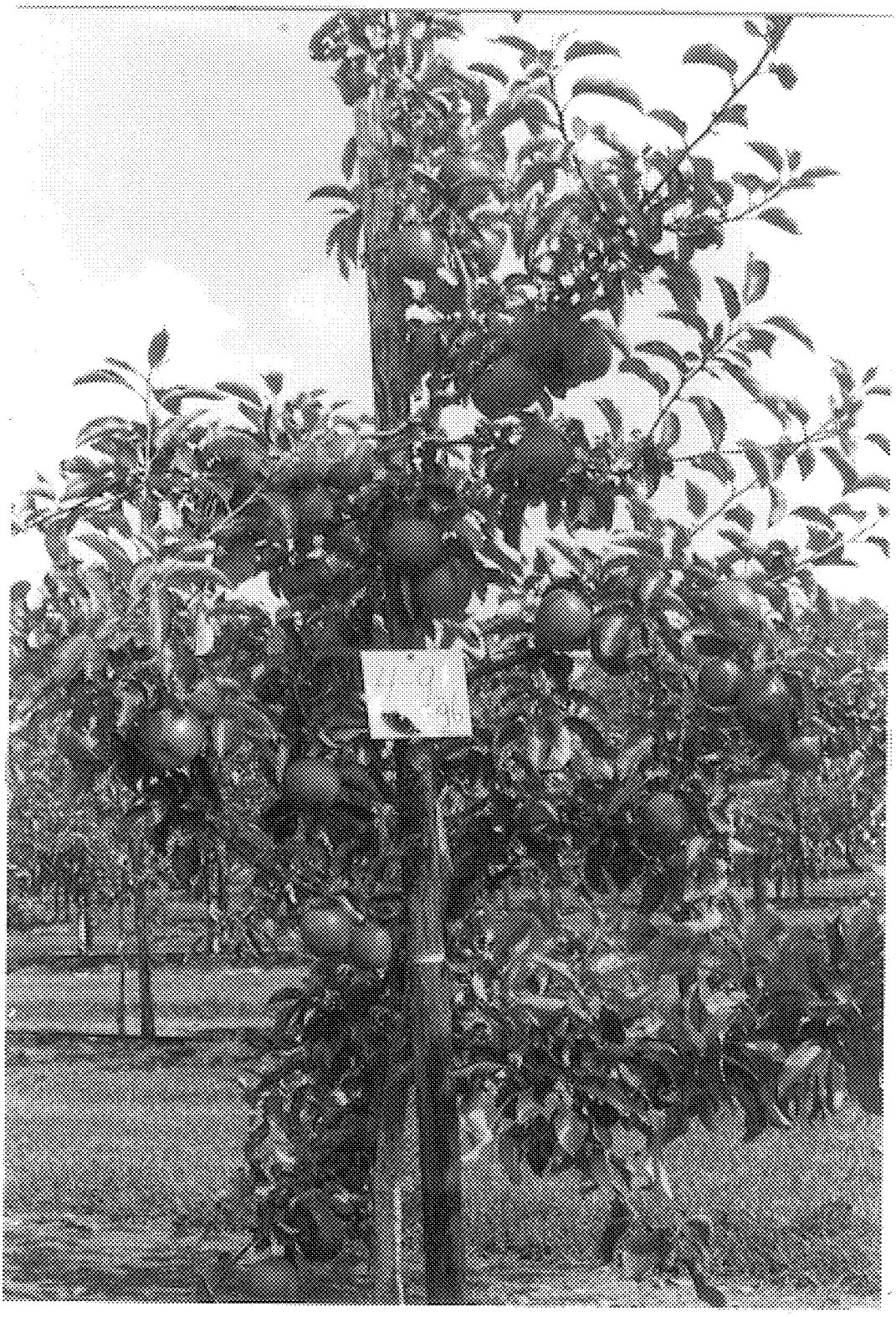
FIG. 1 is a photograph of the apple tree Red Jonaprince as described herein.
Figure 2:
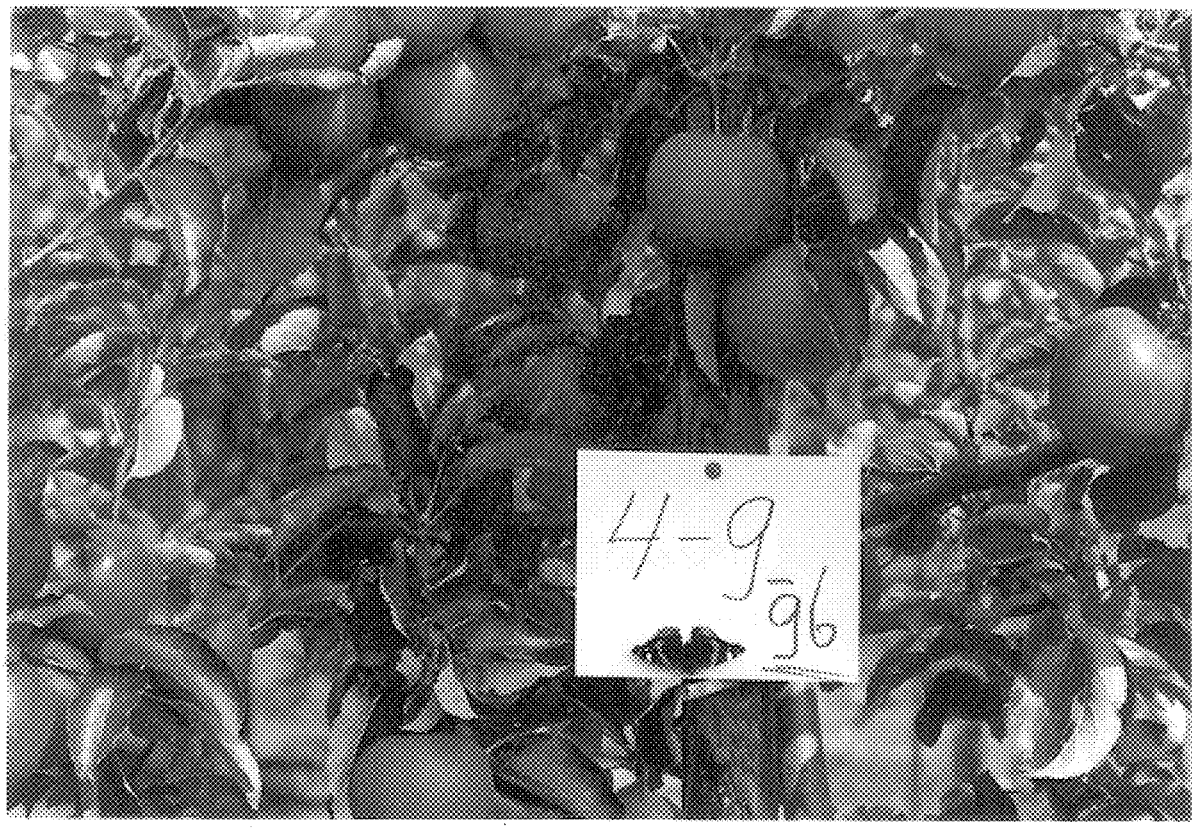
FIG. 2 is a photograph of a close-up of clumps of the Red Jonaprince apples.
Figure 3:
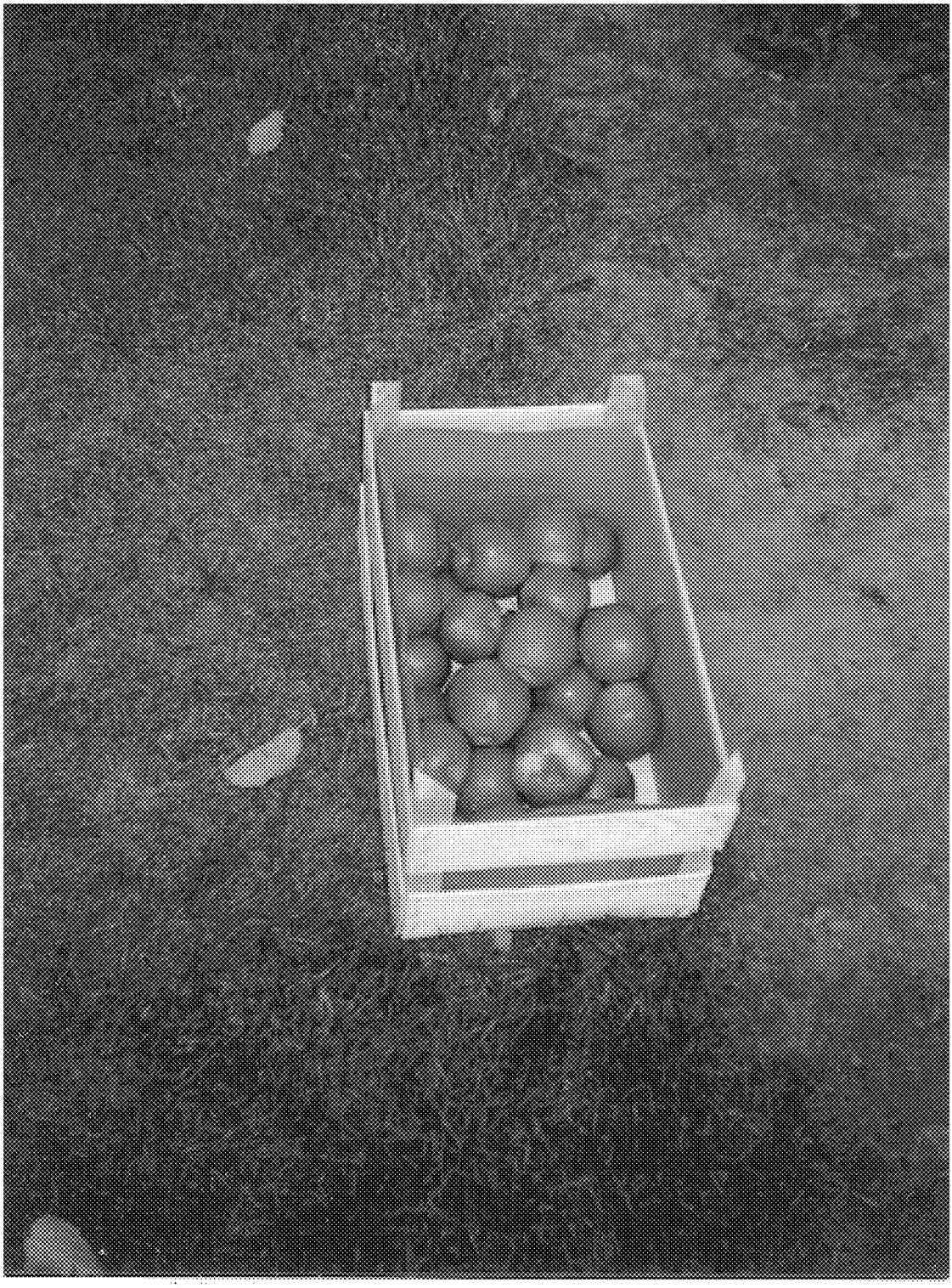
FIG. 3 is a photograph of a container of picked Red Jonaprince apples.

The following detailed descriptions set forth the characteristics of the new variety. The data which define these characteristics were collected from asexual reproductions carried out in Weert, The Netherlands. The color readings were taken in natural light. Color references are primarily to the R.H.S. Colour Chart of The Royal Horticulture Society of London.

Botanical name: Malus Mill.
Commercial name: Red Jonaprince.
Tree:
- *Size.*—Medium.
- *Hardiness.*—Relatively hardy.
- *Habit.*—Moderately vigorous growth.
- *Disease resistance.*—Similar to Jonagold.

Trunk:
- *Stoutness.*—Medium.
- *Color.*—Light brown-grey.
- *Texture.*—Smooth.

Branches:
- *Diameter.*—Medium thick; about 2.5 to 3.0 cm.
- *Texture.*—Smooth.
- *Amount of branching.*—Average.
- *Lenticels.*—Quantity: Moderate. Size: Medium large.

Leaves:
- *Length.*—10.5 cm.
- *Width.*—7.5 cm.
- *Shape.*—Oval with a pointed tip and blunt base.
- *Margins.*—Serrate.
- *Thickness.*—Medium.
- *Prominence of ribs.*—Average.
- *Color.*—Upper side: Yellow-Green Group 147A. Under side: Yellow-Green Group 147B. Stalk: Fades from reddish to Greyed-Orange Group 172A on the main vein.

Flowers:
- *Time of full bloom at Weert, The Netherlands.*—Late as compared to others in this market class, same as Jonagold.
- *Size.*—Medium.

*Petal color.*—At the beginning of blooming, pink; at peak of blooming, white on the front side and very light pink blush on the reverse side.

*Receptacle color.*—At the end of flowering period, purple red.

Fruit:

*Shape.*—Generally frustoconical shape, mostly wider than high.

*Length of axis.*—6.5 cm.

*Average height.*—6.5 to 7 cm.

*Average breadth.*—7.5 to 8.5 cm.

*Cavity of stem.*—Width: 2.5 cm. Depth: 1.5 cm.

*Stem.*—Length: 3 cm. Character: Ligneous.

*Skin.*—Texture: Smooth, not greasy. Lenticel color: Cream-white to light yellow.

*Color.*—Ground: Greyed-Yellow Group 160B. Over: Red Group 46A, solid, with 98 percent covering at picking time.

*Calyx.*—Height: 0.9 cm. Breadth: 1.0 cm.

*Eye.*—Blunt, oval shaped.

*Core.*—Size: Medium. Development of seeds: Well developed.

*Flesh.*—Color: Creamy white. Juiciness: Juicy. Texture: Firm and compact cell tissue; small cells. Flavor: Rich and aromatic; long lasting taste on the palate, even after long-term storage. Quality: Excellent and crispy.

*Seeds.*—Number perfect: 10. Number in one cell: 2. Length: 8 mm. Breadth: 3.5 mm. Color: Dark brown.

*Time of maturity.*—Same as Jonagold, early September.

*Keeping quality.*—One full year immediately after harvest.

*Pollination.*—A donator standing nearby is preferable; comparable with Jonagold.

We claim:

1. A new and distinct variety of apple tree named Red Jonaprince as described and illustrated, and particularly characterized by its relatively early ripening and bright to dark red colored, non-greasy apple.

* * * * *